(12) United States Patent
Detwiler et al.

(10) Patent No.: US 6,797,138 B1
(45) Date of Patent: Sep. 28, 2004

(54) GAS SENIOR DESIGN AND METHOD FOR FORMING THE SAME

(75) Inventors: Eric J. Detwiler, Davison, MI (US); Jeffrey T. Coha, Greenwood, IN (US); Da Yu Wang, Troy, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/089,766

(22) PCT Filed: Oct. 20, 2000

(86) PCT No.: PCT/US00/29147
§ 371 (c)(1),
(2), (4) Date: Aug. 14, 2002

(87) PCT Pub. No.: WO01/29552
PCT Pub. Date: Apr. 26, 2001

Related U.S. Application Data
(60) Provisional application No. 60/160,733, filed on Oct. 20, 1999.

(51) Int. Cl.[7] .............................................. G01N 27/407
(52) U.S. Cl. ...................... 204/427; 204/424; 204/426; 264/44; 264/618
(58) Field of Search ............................ 204/421–429; 264/44, 618

(56) References Cited

U.S. PATENT DOCUMENTS

| | | | |
|---|---|---|---|
| 4,107,019 A | * | 8/1978 | Takao et al. |
| 4,655,901 A | * | 4/1987 | Mase et al. |
| 4,657,659 A | * | 4/1987 | Mase et al. |
| 4,900,425 A | * | 2/1990 | Sasayama et al. |
| 5,169,512 A | * | 12/1992 | Wiedenmann et al. |
| 5,304,294 A | * | 4/1994 | Wang et al. |
| 5,384,030 A | * | 1/1995 | Duce et al. |
| 5,529,677 A | * | 6/1996 | Schneider et al. |
| 5,976,350 A | * | 11/1999 | Yamada et al. |
| 6,227,033 B1 | | 5/2001 | Kainz |
| 6,287,439 B1 | * | 9/2001 | Kato et al. |
| 6,382,198 B1 | | 5/2002 | Smith et al. |
| 6,453,726 B1 | | 9/2002 | Gutierrez et al. |
| 6,484,561 B2 | | 11/2002 | Jackson et al. |
| 6,514,397 B2 | | 2/2003 | LaBarge et al. |
| 6,544,467 B2 | | 4/2003 | Symons et al. |
| 6,562,747 B2 | | 5/2003 | Symons et al. |
| 6,579,435 B2 | | 6/2003 | Wang et al. |
| 6,579,436 B2 | | 6/2003 | Wang et al. |
| 6,585,872 B2 | | 7/2003 | Donelon et al. |
| 6,666,962 B2 | * | 12/2003 | Neumann et al. ........... 204/427 |

FOREIGN PATENT DOCUMENTS

| DE | 19835766 | * | 2/2000 |
|---|---|---|---|

* cited by examiner

Primary Examiner—Kaj K. Olsen
(74) Attorney, Agent, or Firm—Jimmy L. Funke

(57) ABSTRACT

A gas sensor comprises a first electrode and a reference electrode with an electrolyte disposed therebetween, wherein the first electrode and said reference electrode are in ionic conmmunication, wherein the reference electrode has a surface on a side of the reference electrode opposite the electrolyte and the surface has a surface area. The gas sensor also comprises a reference gas channel in fluid communication with the reference electrode, wherein at least a portion of the surface of the reference electrode physically contacts at least a portion of the reference gas channel, and wherein the portion of the reference electrode in physical contact with the reference gas channel is less than about 90% of the surface area.

26 Claims, 2 Drawing Sheets

GAS SENIOR DESIGN AND METHOD FOR FORMING THE SAME

CROSS REFERENCE TO RELATED APPLICATIONS

This case claims the benefit of the filing date of the provisional application U.S. Provisional Application Serial No. 60/160,733 filed Oct. 20, 1999, which is hereby incorporated by reference in its entirety.

TECHNICAL FIELD

This invention relates to gas sensors, and, more particularly, to oxygen sensors.

BACKGROUND OF THE INVENTION

Oxygen sensors are used in a variety of applications that require qualitative and quantitative analysis of gases. In automotive applications, the direct relationship between the oxygen concentration in the exhaust gas and the air-to-fuel ratio of the fuel mixture supplied to the engine allows the oxygen sensor to provide oxygen concentration measurements for determination of optimum combustion conditions, maximization of fuel economy, and the management of exhaust emissions.

A conventional stoichiometric oxygen sensor typically comprises an ionically conductive solid electrolyte material, a porous electrode on the exterior surface of the electrolyte exposed to the exhaust gases with a porous protective overcoat, and an electrode on the interior surface of the sensor exposed to a known oxygen partial pressure. Sensors typically used in automotive applications use a yttria stabilized zirconia based electrochemical galvanic cell with platinum electrodes, which operate in potentiometric mode to detect the relative amounts of oxygen present in the exhaust of an automobile engine. When opposite surfaces of this galvanic cell are exposed to different oxygen partial pressures, an electromotive force is developed between the electrodes on the opposite surfaces of the zirconia wall, according to the Nernst equation:

$$E = \left(\frac{RT}{4F}\right)\ln\left(\frac{P_{O_2}^{ref}}{P_{O_2}}\right)$$

where:
E=electromotive force
R=universal gas constant
F=Faraday constant
T=absolute temperature of the gas
$P_{O_2}^{ref}$=oxygen partial pressure of the reference gas
$P_{O_2}$=oxygen partial pressure of the exhaust gas Due to the large difference in oxygen partial pressure between fuel rich and fuel lean exhaust conditions, the electromotive force (emf) changes sharply at the stoichiometric point, giving rise to the characteristic switching behavior of these sensors. Consequently, these potentiometric oxygen sensors indicate qualitatively whether the engine is operating fuel-rich or fuel-lean, conditions without quantifying the actual air-to-fuel ratio of the exhaust mixture.

The internal resistance of a gas sensor significantly impacts the sensors performance. Areas affected include: light off time, steady state offset voltage, voltage output levels, and "loading down" effect of input impedance. The internal resistance of a gas sensor is comprised of three components: the linear electrolyte resistance, the nonlinear reference electrode polarization (overpotential), and the exhaust gas electrode polarization (overpotential). The first two components play a dominant role in the internal resistance, while the exhaust gas electrode polarization is not as important.

The linear electrolyte resistance and the nonlinear reference electrode polarization affect sensor performance because of the high electrical charge exchange rate with the electrolyte when platinum is used as the electrode. material. Because of this, the size of the electrodes, particularly the reference electrode plays an important role in determining the overall impedance of the sensor. Conventional reference electrodes are manufactured as large as the air reference chamber (as large as possible) due to the fear that the electrode would polarize due to diffusion limiting. Therefore, the impedance of the sensor would be large due to the small reference electrode.

Other sensor designs have attempted to lower the impedance of the sensor by having dual lower shields, a higher wattage heater, a lower mass element, or by reducing the zirconia thickness. However, although these methods reduce impedance, these processes are limited and tend to affect sensor performance.

What is needed in the art is an improved reference electrode that reduces impedance.

BRIEF SUMMARY OF THE INVENTION

The deficiencies of the above-discussed prior art are overcome or alleviated by the gas sensor and method of producing the same.

In a preferred embodiment, a gas sensor comprises a first electrode and a reference electrode with an electrolyte disposed therebetween, wherein the first electrode and said reference electrode are in ionic communication, wherein the reference electrode has a surface on a side of the reference electrode opposite the electrolyte and the surface has a surface area. The gas sensor also comprises a reference gas channel in fluid conmmunication with the reference electrode, wherein at least a portion of the surface of the reference electrode physically contacts at least a portion of the reference gas channel, and wherein the portion of the reference electrode in physical contact with the reference gas channel is less than about 90% of the surface area.

In a preferred method, a gas sensor is formed by disposing an outer electrode and a reference electrode on opposite sides of an electrolyte such that the outer electrode and the reference electrode are in ionic communication, wherein the reference electrode has a surface on a side of the reference electrode opposite the electrolyte. Disposing at least a portion of a fugitive material in physical contact with a portion of the reference electrode surface, wherein the reference electrode has a surface area and the portion of the reference electrode surface in physical contact with the fugitive material is less than about 90% of the surface area. Disposing a heater on a side of the fugitive material opposite the reference electrode to form a green sensor and co-firing the green sensor.

The above-described and other features and advantages of the present invention will be appreciated and understood by those skilled in the art from the following detailed description, drawings, and appended claims.

BRIEF DESCRIPTION OF THE DRAWINGS

The apparatus and method will now be described by way of example, with reference to the accompanying drawing, which is meant to be exemplary, not limiting.

DETAILED DESCRIPTION OF THE INVENTION

Although the gas sensor will be described in relation to an oxygen sensor, it is understood that the novelties disclosed herein can be applied to any gas sensor, including, but not limited to nitrogen oxide sensors, hydrocarbon sensors, carbon monoxide sensors, and hydrogen sensors.

The gas sensor comprises one or more electrochemical cells (i.e., an electrolyte disposed between two electrodes), with a heater in thermal communication with the electrochemical cell(s). In a single cell design, a porous protective layer is typically disposed adjacent to an outer electrode, with a reference gas chamber disposed in fluid communication with both a reference electrode and the atmosphere around the gas sensor, i.e., the air and, optionally the exhaust gas. In order to seal the reference gas chamber from exposure to the exhaust gas, it may optionally be hermetically sealed. Additionally, one or more gas diffusion limiters may be employed within the reference gas chamber as an alternative to or in conjunction with a hermetic seal.

Figure 1:
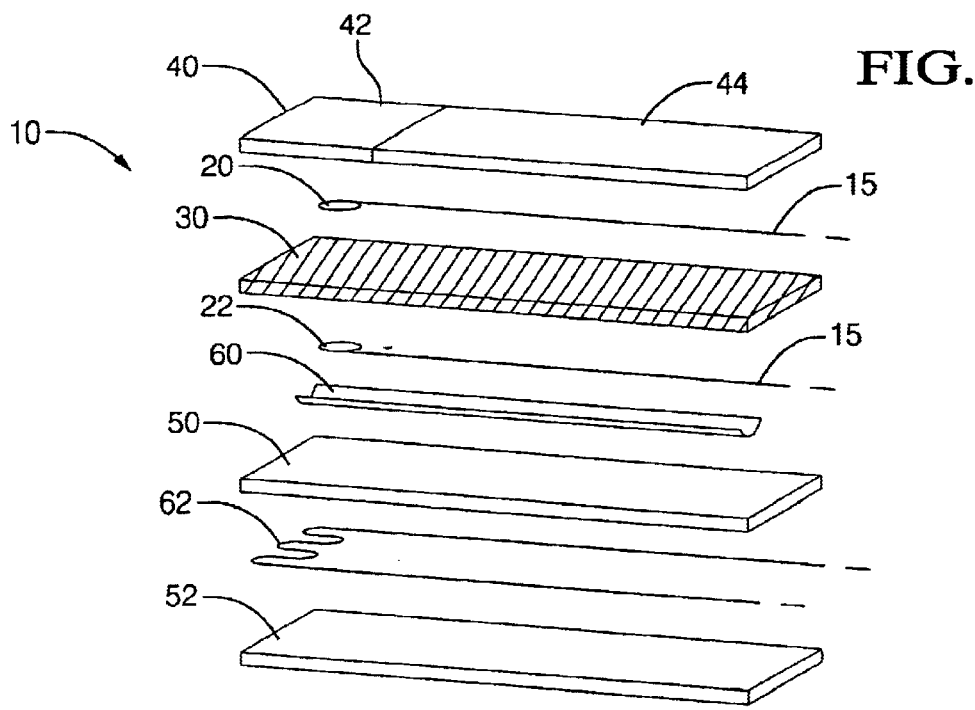
FIG. 1 is an expanded view of a sensor design.

Referring to FIG. 1, the sensor element 10 is illustrated. The exhaust gas (or outer) electrode 20 and the reference gas (or inner) electrode 22 are disposed on opposite sides of, and adjacent to, a solid electrolyte layer 30 creating an electrochemical cell (20/30/22). On the side of the exhaust gas electrode 20 opposite solid electrolyte 30 is a protective insulating layer 40 having a dense section 44 and a porous section 42 that enables fluid communication between the exhaust gas electrode 20 and the exhaust gas. Meanwhile, disposed on the side of the reference electrode 22, opposite the solid electrolyte 30, is a reference gas channel 60 that is in fluid communication with the reference electrode 22 and optionally with the ambient atmosphere and/or the exhaust gas. Disposed on a side of the reference gas channel 60, opposite the reference electrode 22, is a heater 62 for maintaining sensor element 10 at the desired operating temperature. Typically disposed between the reference gas channel 60 and the heater 62, as well as on a side of the heater opposite the reference gas channel 60, are one or more insulating layers 50, 52.

Insulating layers 50, 52, and any support layers, are typically capable of: providing structural integrity (e.g., effectively protecting various portions of the gas sensor from abrasion, vibration, and the like, and providing physical strength to the sensor); and physically separating and electrically isolating various components. The insulating layer (s), which can be formed using ceramic tape casting methods or other methods such as plasma spray deposition techniques, screen printing, stenciling and others conventionally used in the art, can each be up to about 200 microns thick, with a thickness of about 50 microns to about 200 microns preferred. Typically these insulating layers comprise a dielectric material, such as alumina and the like. Since the materials employed in the manufacture of gas sensors preferably comprise substantially similar coefficients of thermal expansion, shrinkage characteristics, and chemical compatibility in order to minimize, if not eliminate, delamination and other processing problems, the particular material, alloy or mixture chosen for the insulating layer is dependent upon the specific electrolyte employed.

The electrolyte layer, which is preferably a solid electrolyte that can comprise the entire layer 30 or a portion thereof, can be any material that is capable of permitting the electrochemical transfer of oxygen ions while inhibiting the physical passage of exhaust gases, has an ionic/total conductivity ratio of approximately unity, and is compatible with the environment in which the gas sensor will be utilized (e.g., up to about 1,000° C.). Possible solid electrolyte materials can comprise any material conventionally employed as sensor electrolytes, including, but not limited to, zirconia which may optionally be stabilized with calcium, barium, yttrium, magnesium, aluminum, lanthanum, cesium, gadolinium, and the like, as well as combinations comprising at least one of the foregoing. For example, the electrolyte can be alumina and yttrium stabilized zirconia. Typically, the solid electrolyte, which can be formed via many conventional processes (e.g., die pressing, roll compaction, stenciling and screen printing, tape casting techniques, and the like), has a thickness of up to about 500 microns, with a thickness of approximately 25 microns to about 500 microns preferred, and a thickness of about 50 microns to about 200 microns especially preferred.

In some embodiments, a porous electrolyte may also be employed. The porous electrolyte should be capable of permitting the physical migration of exhaust gas and the electrochemical movement of oxygen ions, and should be compatible with the environment in which the gas sensor is utilized. Typically, a porous electrolyte has a porosity of up to about 20%, with a median pore size of up to about 0.5 microns, or, alternatively, comprises a solid electrolyte having one or more holes, slits, or apertures therein, so as to enable the physical passage of exhaust gases. Commonly assigned U.S. Pat. No. 5,762,737 to Bloink et al., which is hereby incorporated in its entirety by reference, further describes porous electrolytes that may be useful in the instant application. Possible porous electrolytes include those listed above for the solid electrolyte.

It should be noted that the electrolyte 30, as well as the protective material 40, can comprise entire layer or any portion thereof; e.g. they can form the layer, be attached to the layer (protective material/electrolyte abutting a dielectric material), or disposed in an opening in the layer (protective material/electrolyte can be an insert in an opening in a dielectric material layer). The latter arrangement eliminates the use of excess electrolyte and protective material, and reduces the size of gas sensor by eliminating layers. Any shape can be used for the electrolyte and protective material, with the size and geometry of the various inserts, and therefore the corresponding openings, is dependent upon the desired size and geometry of the adjacent electrodes. It is preferred that the openings, inserts, and electrodes have a substantially similar geometry.

Disposed on opposites sides of the electrolyte 30, and in ionic communication therewith, are electrodes 20, 22. These electrodes can comprise any catalyst capable of ionizing oxygen, including, but not limited to, metals such as platinum, palladium, osmium, rhodium, iridium, gold, and ruthenium; metal oxides such as zirconia, yttria, ceria, calcia, alumina and the like; other materials, such as silicon, and the like; and mixtures and alloys comprising at least one of the foregoing catalysts. As with the electrolyte, the electrodes 20, 22 can be formed using conventional techniques. Some possible techniques include sputtering, chemical vapor deposition, screen printing, and stenciling, among others. If a co-firing process is employed for the formation of the sensor, screen printing the electrodes onto appropriate tapes is preferred due to simplicity, economy, and compatibility with the co-fired process. For example, reference electrode 22 can be screen printed onto insulating layer 50 or over the solid electrolyte 30, while exhaust electrode 20 can be screen printed over solid electrolyte 30 or on protective layer 40. Electrode leads 15 and vias (not shown) in the insulating and/or electrolyte layers are typically formed simultaneously with electrodes.

In order to reduce offset voltage, i.e., reduce impedance, the size (e.g., diameter) of the reference electrode can be different, preferably larger, than the diameter of the exhaust gas electrode. Previously it was believed that the portion of the reference electrode which did not overlap the reference gas channel would be inactive. Consequently, the reference electrode, to minimize resistance, had a diameter substantially equivalent to the width of the reference gas channel. It has been discovered, however, that a reduction in impedance can be obtained by increasing the size of the reference electrode with the ultimate size merely bounded by the size of the layer upon which the electrode is disposed. For example, the reference electrode can have a diameter which is up to about 95% of the width ("w") of the insulating layer, with a width about 60% to about 85% of the width of the support layer preferred, and a width of about 70% to about 80% of the width of the support layer especially preferred. Essentially, the reference electrode has a surface disposed on a side of the reference electrode opposite the electrolyte. At least a portion of the reference electrode surface is in physical contact with the reference gas channel. The portion of the surface in contact with the reference gas channel can be up to about 90% of the reference electrode surface area, with about 75% or less, about 50% or less, about 25% or less, and even 15% or less, of the reference electrode surface area acceptable.

In order to ensure sufficient diffusion of the reference gas through the reference electrode, the reference electrode preferably has a sufficient porosity such that the mass diffusion, i.e., the combined gas and solid transport, of the reference gas to the triple points is not reaction limiting. In other words, there is sufficient oxygen available at the triple points such that the sensor readings are not affected. As is known in the art, the reference electrode porosity can be controlled via a number of factors including the size of the particles employed to form the electrode, the use of fugitive materials, etc. Typically the electrodes comprise any catalyst capable of ionizing oxygen, including, but not limited to, precious metal catalysts such as platinum, palladium, gold, rhodium, and the like, other metals and metal oxides, and other conventional catalysts including mixtures and alloys comprising at least one of these materials. In order to ensure the desired porosity, the catalyst employed for the reference electrode preferably has an average particle size of about 10 microns ($\mu$) or less.

Disposed in fluid communication with the reference electrode 22 is the reference gas channel 60. This channel can be contained within the sensor, can be in fluid communication with air or other reference gas external to the sensor with a hermetic seal to prevent poisoning by the exhaust gas, or can be in fluid communication with the exhaust gas. Production of the reference gas channel can be accomplished via mechanical cutting-in duck, screen-printing fugitive material (such as carbon which can be burned off at high temperature), porosity controlled coating layering, laser drilling holes, and the like. For example, the reference gas channel 60 can be formed by depositing a fugitive material (e.g., carbon base material such as carbon black), between reference electrode 22 and layer 50 such that upon processing the carbon burns out, and leaves a void. Optionally, the reference gas channel 60 can have a controlled geometry to impart diffusion limitation therein (e.g., a small cross-sectional area which inhibits exhaust gas migration into the channel while allowing escape of excess oxygen), and/or can comprise an oxygen storage material to ensure sufficient oxygen supply to the reference electrode 22. Some examples of possible oxygen storage materials include precious metals, as well as alloys and mixtures comprising at least one precious metal.

On a side of the reference gas channel 60 opposite the reference electrode 22, typically disposed between two insulating layers, e.g., 50, 52, is a heater 62 that is employed to maintain the sensor element at the desired operating temperature. Heater 62 can be any conventional heater capable of maintaining the sensor end at a sufficient temperature to facilitate the various electrochemical reactions therein. The heater 62, which is typically platinum, alumina, palladium, and the like, as well as mixtures and alloys comprising at least one of the foregoing metals, or any other conventional heater, is generally screen printed onto a substrate to a thickness of about 5 microns to about 50 microns.

As with the heater 60, other conventional gas sensor components and/or materials can be employed, such as ground plane(s), lead gettering layer(s), additional support layer(s), additional electrochemical cell(s), vias, contact pads, protective coating(s), and the like. For example, protective coatings (e.g., spinel, alumina, magnesium aluminate, and the like, as well as combinations comprising at least one of the foregoing coatings), can be disposed over the sensor or merely over one or more of the outer layers (i.e., protective layer 40 and/or insulating layer 52).

Basically, formation of the gas sensor can be accomplished in any conventional fashion; e.g., forming the individual layers of the sensor, firing the layers, and stacking the layers to for the sensor, or forming the green layers, stacking the layers, and co-firing to produce the sensor. For example, a protective layer, three insulating layers, an electrolyte layer, and a porous layer are formed using a doctor blade tape forming method. The desired vias are formed in these layers accordingly. Holes are also formed in the protective layer and the electrolyte layer using a punching technique. Inserts are formed from the electrolyte layer and the porous layer using a similar punching technique, wherein the inserts size and geometry is preferably substantially the same as the hole size and geometry. The porous insert is then disposed into the protective layer hole and the electrolyte insert is disposed in the insulating layer hole. An exhaust gas electrode is then screen printed over the electrolyte with a lead printed across the insulating layer. On another insulating layer a fugitive material is sputtered across the layer and then a reference electrode is screen printed at one end of the insulating layer in fluid communication with the fugitive material, and a lead is printed down the insulating layer. On the final insulating layer a heater with heater leads is printed. The layers are then stacked accordingly (e.g., see FIG. 1), and contacts are formed on the outer surfaces of the sensor. The sensor can then optionally be dipped to apply a protective coating on the sensor. Finally, the green sensor is laminated at about 2,000 to about 4,000 pounds per square inch (psi) and at temperatures up to about 70° C. or so, singulated, and co-fired at atmospheric pressure and temperatures up to about 1550° C. or so.

Figure 2:
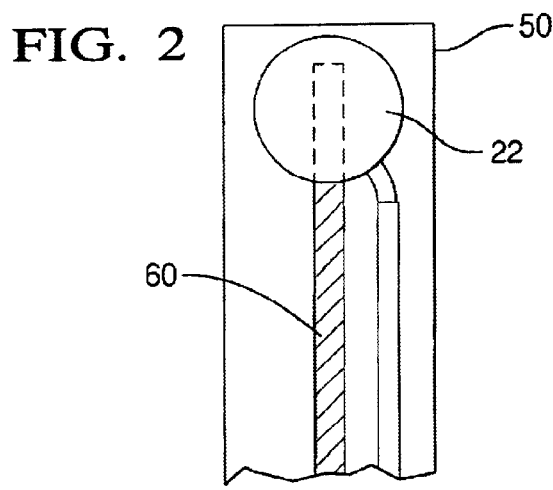
FIG. 2 is a view of a exemplary design of a reference electrode and a reference gas channel.

Referring to FIG. 2, insulating layer 50 with reference gas channel 60 and reference electrode 22 disposed thereon is illustrated. As is evident from the figure, the reference electrode 22 is substantially larger than the reference gas channel 60, with the channel 60 only overlapping less than about 20% of the reference electrode 22.

Figure 3:
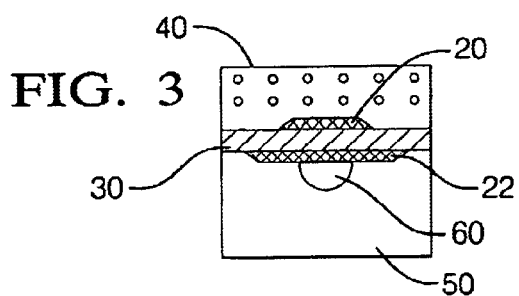
FIG. 3 is a cross-sectional view of a sensor design.
Figure 4:
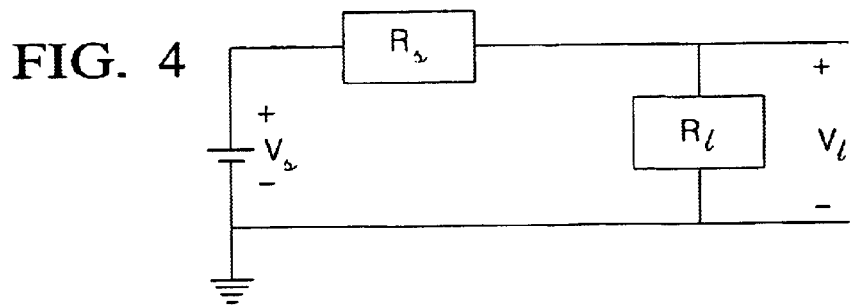
FIG. 4 is a circuit diagram for a sensor.

A cross-sectional view of a sensing element employing the reference electrode of FIG. 2 is presented in FIG. 3. FIG. 3 illustrates that the reference electrode 22 does not have to be limited in size by the reference gas channel 60 and that the electrodes do not need to have the same diameter. Due to the chemistry of the reaction, it is not necessary to increase the size of the exhaust gas electrode 20 (actually, increasing the size merely increases cost with little to no benefit) while increasing the size of the reference electrode 22 substantially reduces the impedance of the sensor. Essentially, by increasing the size of the reference electrode, the impedance can be reduced by greater than 25% versus conventional sensors having reference electrodes having about 95% overlap with the air reference channel or greater. Consequently, the reference electrode 22 can be a different size than the exhaust gas electrode 20, with a larger reference electrode preferred.

The following examples are merely intended to further illustrate the invention and not to limit the scope thereof.

EXAMPLE 1

Alumina and yttria-doped zirconia were mixed with binders, plasticizers, and solvents. They were roll-milled into a slurry. The slurry was casted into thick film tapes by doctor blade tape casting method. Platinum inks and carbon inks were screen printed onto the tapes in the structure as shown in FIG. 1. Protective layer 40 was a composite layer of alumina and porous tape which contained various mixtures of carbon, zirconia, and alumina. Layers 50, 52 were alumina tapes for insulation and support. Layer 30 was the solid electrolyte layer (i.e., yttria-doped zirconia). Screen prints 20, 22 were the exhaust and reference electrodes, respectively. These prints are platinum with various additives (i.e., zirconia, carbon). Screen print 62 is the integrated resistive heater. It is a platinum print with alumina powder added. Screen print 60 is a carbon print which is fugitive material. Therefore, after sintering, this is an open chamber.

After each layer was processed, they were stacked properly, laminated, singulated, and fired at 1,500° C.

Figure 5:
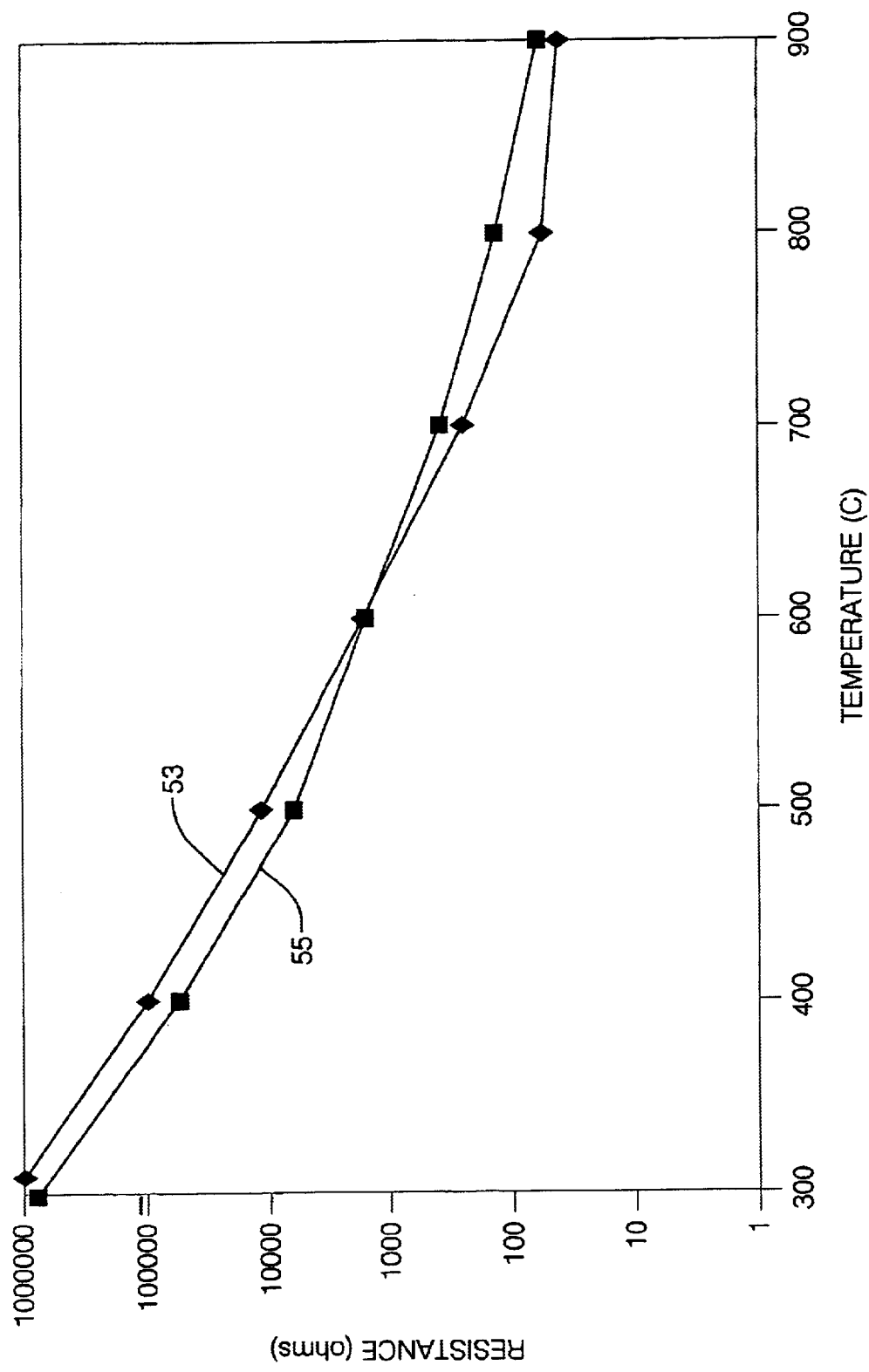
FIG. 5 is a graphical representation of sensor resistance in comparison to model resistance over a range of temperatures.

The impedance of the sample was measured by applying a voltage to the heater until a temperature of about 800° C. to about 900° C. was reached. A small, constant bias voltage was then applied to the electrochemical cell, and the resulting current was measured. FIG. 5 is a graphical representation of the results (line 53), along with the theoretical calculations (line 55) for what the impedance should be at the corresponding temperatures. The equation for the DC impedance of an electrochemical cell is set forth in Equation (I) as follows:

$$R_{zirconia} = p*(L/A) \tag{I}$$

where: p—resistivity of electrolyte

L—thickness of electrolyte

A—area of electrode

The resistivity factor (p) is described by the following Equation (II):

$$p = 10^{-5} \left( e^{\frac{Lev}{kT}} \right) T \tag{II}$$

where: T—temperature (Kelvin)

K—8.63* $10^{-5}$ (Boltzmann's constant)

Lev—activation energy of zirconia (fundamental property of material)

$10^5$—ionic mobility

The above Equations I and II assume that the entire reference electrode will be active. Yet, only a small amount of the reference electrode must be exposed to the reference gas channel, and the reference electrode will not diffusion-limit the flow of oxygen. Therefore, essentially all of the reference electrode area is active, and the above equations apply. The reference gas channel can be created as small as possible while the reference electrode can be increased, thus lowering the electrolyte resistance and the reference electrode polarization.

EXAMPLE 2

Two sensors were formed using conventional techniques: a wide reference electrode sensor having a 3 mm diameter disk (area of about 7 mm$^2$) (Sample A); and a conventional sensor having a "thin" reference electrode (0.5 millimeters (mm) wide and 5 mm long rectangle (area of about 2.5 mm$^2$) (Sample B); both sensors had a reference gas channel which was about 0.6 mm wide and about 5.5 mm long. The remainder of the sensor components, protective layer, insulating layers, exhaust gas electrode, heater, electrolyte, etc., which were conventional, were the same for both sensors.

Resistance of these sensors was then determined. First, the sensors were maintained in a fuel rich environment (e.g., an air to fuel (A/F) ratio of about 13.3) to generate an electromotive force (emf). Next, a small load resistor (about 50 kiloohms (kΩ)) was attached to the sensor, demanding a current of:

$$I = \frac{V_s}{R_s + R_l}$$

where: $V_s$=emf $R_s$=internal sensor resistance $R_l$=input impedance of ECM $R_s$ can be calculated from the voltage divides between the resistor and the internal resistance (impedance) of the sensor, the open circuit voltage, the loaded voltage, and the know input impedance of engine control module (ECM). The voltage divider Equation (III) is:

$$V_l = V_s \left( \frac{R_l}{R_l + R_s} \right) \tag{III}$$

where: $V_l$=loaded voltage

With testing performed under the same conditions, (e.g., temperature and engine conditions), Sample A had a mean resistance of 3,400 ohms, while Sample B bad a mean resistance of 4,800 ohmns. Basically a sensor was produced having a reduced mean resistance, e.g., below about 4,000 Ω. with below about 3,500 Ω preferred, and about 3,400 Ω or less especially preferred.

Artisans believed that in order for the reference electrode to be effective, it could not be larger than the air reference gas channel in the area of that electrode. Basically, the reference electrode and reference gas channel needed to substantially overlap (e.g., greater than about 95%). It was believed that the portion of the reference electrode, which did not overlap the reference gas channel, would be inactive. This belief posed particular problems for co-fired sensors since the size of the reference gas channel was limited. Essentially, due to the subsequent processing to volatilize the fugitive material (laminating, sintering, and the associated temperatures and pressures), if the channel was too large it would deform (e.g., collapse, pinch off, or the like). Consequently, the size of the reference gas channel was limited due to processing limitations, and hence it was believed that the size of the reference electrode was limited by the size of the channel. Contrary to that belief, however, it has been discovered that, since only a small amount of the reference electrode needs to be exposed to the reference gas channel in order to attain the desired reference gas supply to the reference electrode, the size of the reference electrode is not dependent upon the size of the reference gas channel. Consequently, the reference electrode size can be optimized based upon the overall sensor size (e.g., width of the layer upon which the electrode is disposed). The resulting sensor possesses a reduced electrochemical cell impedance, and performance parameters including rich exhaust voltage, light-off time, and loading down the sensor with the input impedance are improved. While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

We claim:

1. A gas sensor, comprising:
   a first electrode and a reference electrode with an electrolyte disposed therebetween, wherein the first electrode and the reference electrode are in ionic communication, wherein the reference electrode has a surface on a side of the reference electrode opposite the electrolyte and the surface has a surface art; and
   a reference gas channel in fluid communication with the reference electrode, wherein at least a portion of the surface of the reference electrode physically contacts at least a portion of the reference gas channel, and wherein the portion of the reference electrode in physical contact with the reference gas channel is less than about 90% of the surface area.

2. A gas sensor as in claim 1, wherein the portion of the reference electrode in physical contact with the reference gas channel is less than about 75% of the surface area.

3. A gas sensor as in claim 2, wherein the portion of the reference electrode in physical contact with the reference gas channel is less than about 50% of the surface area.

4. A gas sensor as in claim 1, further comprising a heater disposed in thermal communication with the reference electrode.

5. A gas sensor as in claim 1, wherein the gas sensor has an impedance below about 4,000 Ω.

6. A gas sensor as in claim 5, wherein the gas sensor has an impedance below about 3,500 Ω.

7. A gas sensor as in claim 6, wherein the gas sensor has an impedance below about 3,400 Ω.

8. A gas sensor as in claim 1, wherein a first electrode size is different than a reference electrode size.

9. A gas sensor as in claim 8, wherein the first electrode size is smaller than the reference electrode size.

10. A method for forming a gas sensor, comprising:
    disposing an outer electrode and a reference electrode on opposite sides of an electrolyte such that the outer electrode and the reference electrode are in ionic communication, wherein the reference electrode has a surface on a side of the reference electrode opposite the electrolyte;
    disposing at least a portion of a fugitive material in physical contact with a portion of the reference electrode surface, wherein the reference electrode has a surface area and the portion of the reference electrode surface in physical contact with the fugitive material is less than about 90% of the surface area;
    disposing a heater on a side of the fugitive material opposite the reference electrode to form a green sensor; and
    co-firing the green sensor.

11. A method for forming a gas sensor as in claim 10, wherein the portion of the reference electrode surface in physical contact with the fugitive material is less than about 75% of the surface area.

12. A method for forming a gas sensor as in claim 11, wherein the portion of the reference electrode surface in physical contact with the fugitive material is less than about 50% of the surface area.

13. A method for forming a gas sensor as in claim 12, wherein the portion of the reference electrode surface in physical contact with the fugitive material is less than about 25% of the surface area.

14. A method for forming a gas sensor as in claim 13, wherein the portion of the reference electrode surface in physical contact with the fugitive material is less than about 15% of the surface area.

15. A method for fanning a gas sensor as in claim 10, wherein the gas sensor has an impedance below about 4,000 Ω.

16. A method for forming a gas sensor as in claim 15, wherein the gas sensor has an impedance below about 3,500 Ω.

17. A method for forming a gas sensor as in claim 16, wherein the gas sensor has an impedance below about 3,400 Ω or less.

18. A method for forming a gas sensor as in claim 10, wherein the fist electrode and the reference electrode are of different sizes.

19. A gas sensor, comprising:
    a first electrode and a reference electrode with an electrolyte disposed therebetween, wherein the first electrode and the reference electrode arc in ionic communication, wherein the reference electrode has a surface on a side of the reference electrode opposite the electrolyte and the surface has a surface area, and wherein the reference electrode having a reference electrode width and is in contact with an insulating layer having an insulating layer width, wherein the reference electrode width is about 60% to about 85% of the insulating layer width; and
    a reference gas channel in fluid communication with the reference electrode, wherein at least a portion of the surface physically contacts at least a portion of the reference gas channel, and wherein the portion of the reference electrode in physical contact with the reference gas channel is less than about 90% of the surface area.

20. A gas sensor as in claim 19, wherein the portion of the reference electrode in physical contact with the reference gas channel is less than about 25% of the surface area.

21. A gas sensor as in claim 19, wherein the gas sensor has an impedance below about 4,000 Ω.

22. A gas sensor as in claim 19, wherein the reference electrode width is 70% to about 80% of the insulating layer width.

23. A gas sensor as in claim 22, wherein the first electrode size is smaller than the reference electrode size.

24. A gas sensor as in claim 19, wherein a first electrode size is different than a reference electrode size.

25. A gas sensor, comprising:
- a first electrode and a reference electrode with an electrolyte disposed therebetween, wherein the first electrode and the reference electrode are in ionic communication, wherein the reference electrode has a surface on a side of the reference electrode opposite the electrolyte and the surface has a surface area; and
- a reference gas channel in fluid communication with the reference electrode, wherein at least a portion of the surface of the reference electrode physically contacts at least a portion of the reference gas channel, and wherein the portion of the reference electrode in physical contact with the reference gas channel is less than about 25% of the surface area.

26. A gas sensor as in claim 25, wherein the portion of the reference electrode in physical contact with the reference gas channel is less than about 15% of the surface area.

* * * * *

UNITED STATES PATENT AND TRADEMARK OFFICE
CERTIFICATE OF CORRECTION

PATENT NO.    : 6,797,138 B1
DATED         : September 28, 2004
INVENTOR(S)   : Detwiler et al.

It is certified that error appears in the above-identified patent and that said Letters Patent is hereby corrected as shown below:

Title page,
Item [54], Title, should read as follows: -- GAS SENSOR DESIGN AND METHOD FOR USING THE SAME --

Signed and Sealed this

Fourth Day of January, 2005

JON W. DUDAS
*Director of the United States Patent and Trademark Office*